US009546393B2

(12) United States Patent
Williamson et al.

(10) Patent No.: US 9,546,393 B2
(45) Date of Patent: Jan. 17, 2017

(54) MASS SPECTROMETRY QUANTITATION OF P450 ISOFORMS IN HEPATOCYTES

(71) Applicant: DH Technologies Development Pte. Ltd., Singapore (SG)

(72) Inventors: Brian L. Williamson, Ashland, MA (US); Subhasish Purkayastha, Acton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/602,917

(22) Filed: Jan. 22, 2015

(65) Prior Publication Data

US 2015/0140600 A1 May 21, 2015

Related U.S. Application Data

(62) Division of application No. 12/904,520, filed on Oct. 14, 2010, now Pat. No. 8,940,545.

(60) Provisional application No. 61/252,648, filed on Oct. 17, 2009, provisional application No. 61/252,430, filed on Oct. 16, 2009.

(51) Int. Cl.
| | | |
|---|---|---|
| *G01N 24/00* | (2006.01) | |
| *C12Q 1/26* | (2006.01) | |
| *C12N 9/02* | (2006.01) | |
| *G01N 33/68* | (2006.01) | |
| *G01N 33/50* | (2006.01) | |
| *G01N 30/72* | (2006.01) | |
| *G01N 30/88* | (2006.01) | |

(52) U.S. Cl.
CPC .............. *C12Q 1/26* (2013.01); *C12N 9/0077* (2013.01); *G01N 33/502* (2013.01); *G01N 33/5023* (2013.01); *G01N 33/5067* (2013.01); *G01N 33/6848* (2013.01); *G01N 30/7233* (2013.01); *G01N 2030/8831* (2013.01); *G01N 2333/90245* (2013.01); *G01N 2500/04* (2013.01); *G01N 2500/10* (2013.01); *G01N 2500/20* (2013.01); *G01N 2560/00* (2013.01); *Y10T 436/24* (2015.01)

(58) Field of Classification Search
None
See application file for complete search history.

(56) References Cited

U.S. PATENT DOCUMENTS

2007/0092926 A1  4/2007  Alterman et al.
2008/0206737 A1  8/2008  Hunter

FOREIGN PATENT DOCUMENTS

EP       2352021 A1    8/2011

OTHER PUBLICATIONS

Wang et al.,"A gel-free MS-based quantitative proteomic approach accurately measures cytochrome P450 protein concentration in human liver microsomes", Proteomics, First published online Sep. 15, 2008.*
International Search Report from International Patent Application No. PCT/US10/52665, dated Mar. 14, 2011.
International Preliminary Report on Patentability ffrom International Patent Application No. PCT/US10/52665, dated Apr. 17, 2012.
Supplementary European Search Report from European Patent Application 10824088.8, dated Mar. 19, 2013.
European Search Opinion from European Patent Application 10824088.8.
Langenfield et al.: "Quantitative analysis of highly homologous proteins: the challenge of assaying the CYP-ome by mass spectrometry.", Anal Bioanal Chem, vol. 392, No. 6, Nov. 2008 (Nov. 2008), pp. 1123-1134.
Zhang S et al: "Liquid chromatography/tandem mass spectrometry method for simultaneous evaluation of activities of five cytochrome P450s using a five-drug cocktail and application to cytochrome P450 phenotyping studies in rats", Journal of Chromatography B: Biomedical Sciences & Applications, Elsevier, Amsterdam, NL, vol. 871, No. 1, Aug. 1, 2008 , pp. 78-89.
Wu, Genbank Accession No. AAF 13602, 1995.
Redlich et al. "Distinction between Human Cytochrome P450 (CYP) Isoforms and Identification of New Phosphorylation Sites by Mass Spectrometry", Journal of Proteome Research, 7, 4678-4688, 2008.
QTRAP 4000 Brochure, 2010.

* cited by examiner

*Primary Examiner* — Lianko Garyu

(57) ABSTRACT

A method for screening a drug for cytochrome P450 (CYP) induction is provided and can include incubating the drug with a microsome-containing biological sample and then quantitating at least one cytochrome P450 isoform. The isoforms can be selected from 2B6, 3A4, 1A2, and 3A5 isoforms. In some embodiments, the method uses liquid chromatography tandem mass spectrometry (LC-MSMS). A quantitated value can be compared to a threshold value and the drug can be determined to exhibit an acceptable CYP induction potential when the quantitated value does not exceed the threshold value. Isolated peptides are also provided.

2 Claims, 8 Drawing Sheets

MASS SPECTROMETRY QUANTITATION OF P450 ISOFORMS IN HEPATOCYTES

CROSS REFERENCE TO RELATED APPLICATIONS

The present application is a divisional of U.S. application Ser. No. 12/904,520, filed Oct. 14, 2010, which claims the benefit of priority from U.S. Provisional Patent Applications Nos. 61/252,648, filed Oct. 17, 2009, and 61/252,430, filed Oct. 16, 2009, all of which are incorporated herein in their entireties by reference.

FIELD

The present teachings relate to cytochrome P450 enzymes (CYPs) and detection of enzymes using mass spectrometry.

BACKGROUND

Cytochrome P450 enzymes (CYPs) are major drug metabolizing enzymes and experimental pharmaceutical compounds are generally evaluated for their CYP induction potential early in the development process. Measurement of a CYP induction profile in response to a chemical can be used as a fundamental aspect of drug safety evaluation, but expression of these proteins is regulated by transcriptional, post transcriptional and translational mechanisms. As a result, mRNA-based assays are not reliable predictors of CYP induction. Further, CYPs exhibit extensive amino acid sequence homology, particularly within subfamilies, so that P450 protein expression methods are also poorly discriminatory.

SUMMARY

According to various embodiments of the present teachings, a method of quantitating the 1A2, 2B6, 3A4, and 3A5 isoforms of cytochrome P450 enzymes (CYPs) is provided without the need for any chemical labeling. Isoform-specific tryptic peptides can be observed in liquid chromatography-Tandem Mass Spectrometry (LC-MSMS) analysis of samples derived from hepatocytes, for example, in microsomes, along with their optimal Q1 and Q3 transitions. Those observed peptides and transitions, can be used to enable a reliable CYP quantitation of the isoforms 1A2, 2B6, 3A4, and 3A5.

According to various embodiments, a set of peptides and optimal MRM transitions are provided as "house keeping" microsomol proteins whose concentrations are unaffected by drug incubation. The set can be used as normalization proteins for quantitative analysis. In some embodiments, quantitation can be performed by spiking into the sample heavy forms of the isoform-specific peptides, for example, forms that have been enriched with C13 and/or N15. FIG. 1 shows a typical MRM analysis for CYP 1A2, CYP2B6, and CYP3A3/3A4 from human microsomes, wherein some of the isoform-specific peptides have been labeled in FIG. 1. The optimized transitions for each of a set of observed, most sensitive isoform-specific peptides, according to various embodiments of the present teachings, is shown in Tables 1-4 below.

BRIEF DESCRIPTION OF THE DRAWINGS

The present teachings will be described with reference to the accompanying drawings. The drawings are intended to illustrate, not limit, the present teachings.

DETAILED DESCRIPTION

Figure 1:
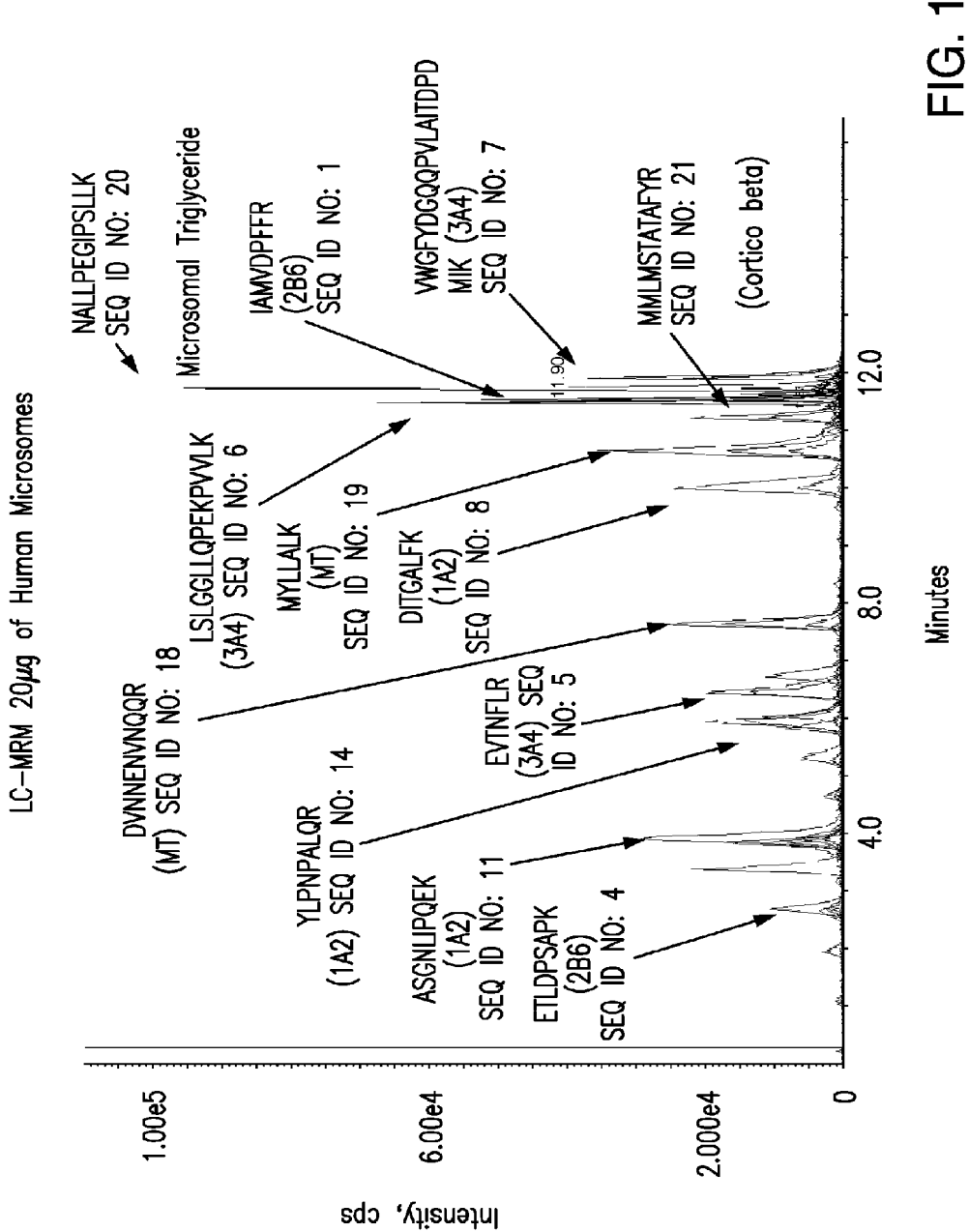
FIG. 1 shows an MRM analysis of 20 μg of a microsomal preparation for CYP 1A2, CYP 2B6, and CYP 3A4 (extracted ion chromatogram (XIC) of +MRM (412 pairs)).

According to various embodiments, a method for screening a drug for cytochrome P450 (CYP) induction is provided that comprises incubating the drug with a microsome-containing biological sample and quantitating at least one CYP isoform. In some embodiments, the isoforms can comprise one or more isoform selected from 2B6, 3A4, 1A2, and 3A5 isoforms. The method can comprise using a liquid chromatography tandem mass spectrometry (LC-MSMS) technique to quantitate the amount of each isoform. The quantitated value of each can be compared to a threshold value, and the drug can be identified as having an acceptable CYP induction potential when the quantitated value does not exceed the threshold value. The threshold value can be selected or predetermined based on a desired CYP induction potential or based on the CYP induction potential of one or more different drugs, similar or non-similar to the drug being screened. In some embodiments, the microsome-containing biological sample can be derived from a mammal, from a primate, or from a human.

According to various embodiments, the drug can be incubated with a sample containing human hepatocytes. In some embodiments, after incubation with the drug, the sample containing human hepatocytes can be used to obtain at least one microsome fraction by, for example, 16 G centrifugation. The microsome fraction can be analyzed for CYP induction by the drug, by detecting isolated peptides specific to CYP (isoform-specific peptides). According to some embodiments, after incubation with the drug, the sample containing human hepatocytes can be used to obtain at least one S9 fraction by, for example, 9 G centrifugation. The S9 fraction can be analyzed to detect CYP induction by the drug, for example, by detecting isolated peptides specific to CYP (isoform-specific peptides). According to some embodiments, the microsome fraction or the S9 fraction can be analyzed using a liquid chromatography tandem mass spectrometry (LC-MSMS) technique in order to quantitate at least one CYP isoform. The quantitated value of each can be compared to a threshold value, and the drug can be identified as having an acceptable CYP induction potential when the quantitated value does not exceed the threshold value.

According to various embodiments, a method is provided for directly analyzing CYP from hepatocytes. In some embodiments, antibody peptides can be used to pull the isoform-specific peptides directly out of hepatocyctes. According to some embodiments, using antibody peptides to pull the isoform-specific peptides directly out of hepatocytes would have the advantage of not needing to prepare S9 or microsome fractions, and would require less hepatocyte cells for drug incubation.

In some embodiments, the method comprises comparing detected induction to a control. For example, because little or no drug induction of CYPs is desirable, a threshold can be set such that the drug must show less than (<) 40% induction compared to the positive control, to be considered acceptable. In some embodiments, the drug must show less than (<) 30% induction compared to the positive control, to be considered acceptable. In other embodiments, the drug must show less than (<) 20% induction compared to the positive control, to be considered acceptable.

According to various embodiments, a method for determining an amount of at least one isoform of cytochrome P450 (CYP) in a sample, is provided. The method can comprise the use of a mass spectrometry technique, wherein the at least one isoform of cytochrome P450 comprises at least one of CYP 2B6, CYP 3A4, CYP 1A2, and CYP 3A5. The mass spectrometry technique can comprise a tandem mass spectrometry (MSMS) technique and/or a liquid chromatography tandem mass spectrometry (LC-MS/MS) technique. In some embodiments, the technique comprises an LC-MS/MS technique and the use of a triple quadrupole instrument and Multiple Reaction Monitoring (MRM).

FIG. 1 shows a typical MRM analysis for CYP 1A2, CYP 2B6, and CYP 3A4, as well as the "housekeeping" microsomal proteins (Microsomal GST, Corticosteroid 11 beta, and Microsomal Tryglyceride), from a microsomal sample preparation prepared as described below in the Examples. The quantity of CYP 1A2, CYP 2B6, and CYP 3A4 can be determined by, for example, Isotope Dilution Mass Spectrometry, wherein the sample preparation is spiked with heavy forms of the isoform-specific peptides. The quantity of CYP 1A2, CYP 2B6, and CYP 3A4 can also be determined using other conventional methods known in the art. In some embodiments, the method uses LC-MSMS with multiple reaction monitoring (MRM) quantitation of the isoform-specific peptides and isotope-coded affinity tags (ICAT) to generate a CYP induction profile. The method can use, for example, approaches similar to the approaches presented by Pennington et at to quantitate isoform-specific cysteine-containing peptides labeled with ICAT as described in *Proteomics*, 6(6), pages 1934-1947 (March 2006), which is incorporated herein in its entirety by reference.

Figure 2:
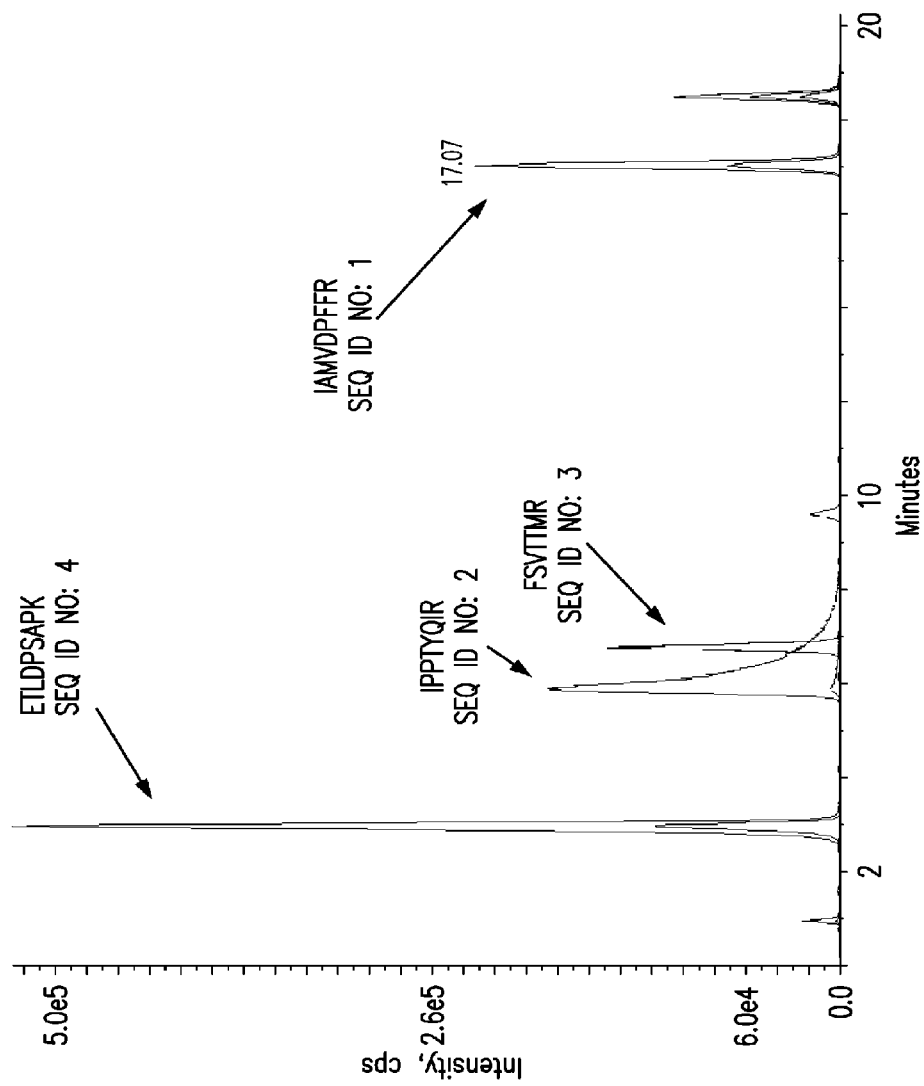
FIG. 2 shows an MRM analysis of 1 μl of a microsomal preparation for CYP 2B6 (extracted ion chromatogram of +MRM (15 pairs)).

FIG. 2 shows a typical MRM analysis for CYP 2B6 from the microsomal preparation prepared as described herein. Isolated peptides comprising the amino acid sequence of SEQ ID NOS: 1, 2, 3, or 4 identified in Table 1 below are specific to CYP 2B6.

Figure 3:
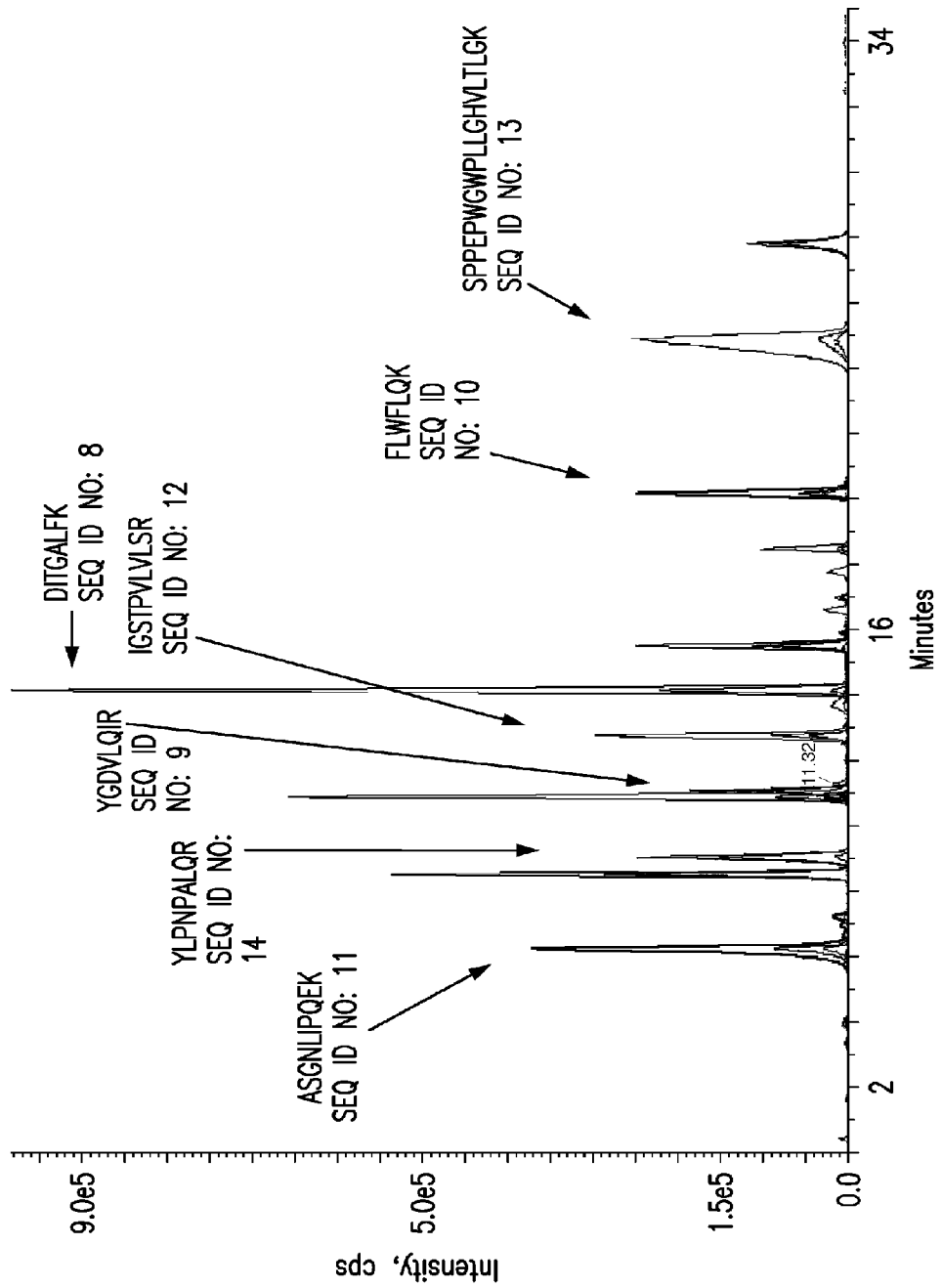
FIG. 3 shows an MRM analysis of 2 μg of a microsomal preparation for CYP 1A2 (extracted ion chromatogram of +MRM (57 pairs)).

FIG. 3 shows a typical MRM analysis for CYP 1A2 from the microsomal preparation prepared as described herein. The isolated peptides comprising the amino acid sequence of SEQ ID NOS: 8, 9, 10, 11, 12, 13, or 14 identified in Table 3 below are specific to CYP 1A2.

Figure 4:
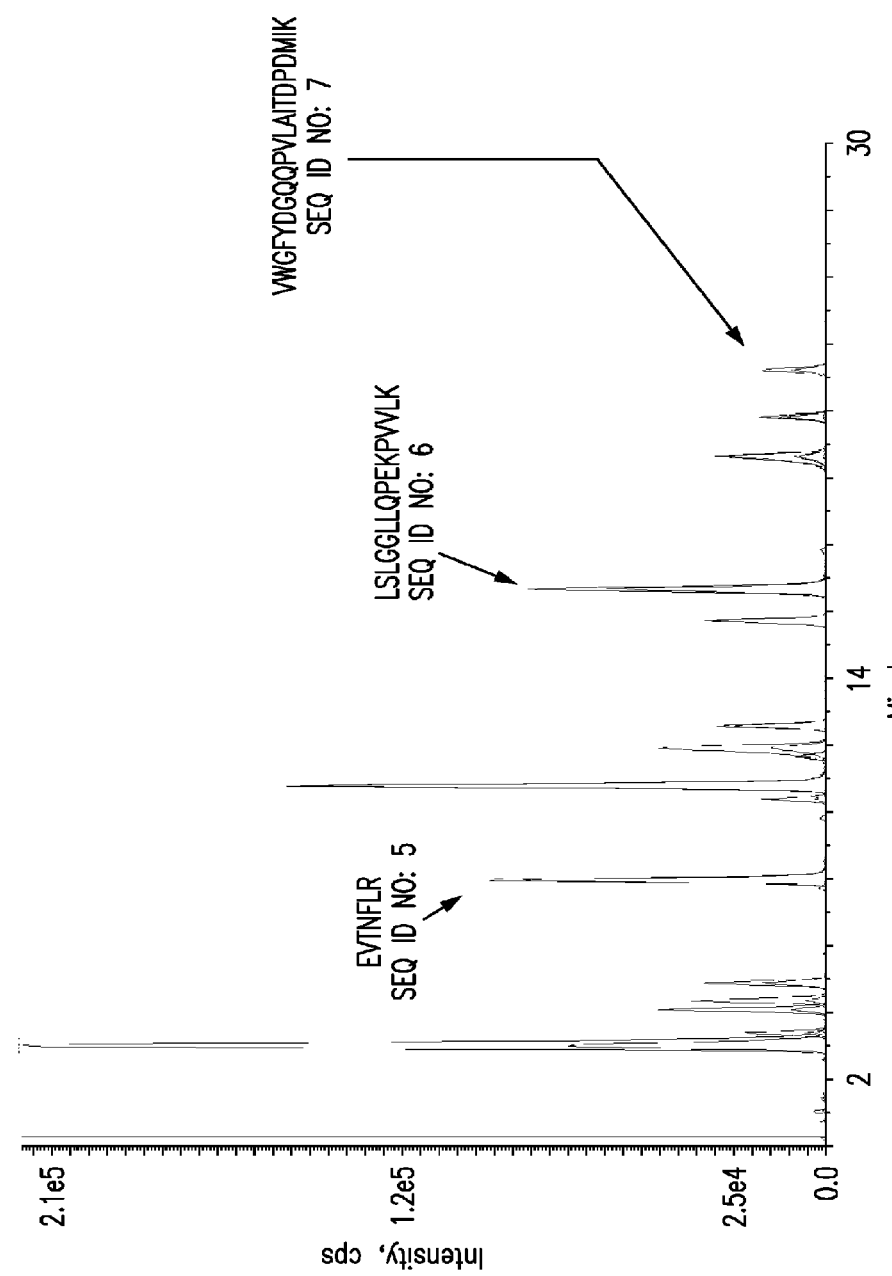
FIG. 4 shows an MRM analysis of 1 μl of a microsomal preparation for CYP 3A4 (extracted ion chromatogram of +MRM (34 pairs)).

FIG. 4 shows a typical MRM analysis for CYP 3A4 from the microsomal preparation prepared as described herein. The isolated peptides comprising the amino acid sequence of SEQ ID NOs: 5, 6, or 7 identified in Table 2 below are specific to CYP 3A4. It should be understood that peptides comprising the amino acid sequence of SEQ ID NOS: 5, 6, or 7 can also be used to identify and/or quantity CYP 3A3.

The isolated peptides comprising the amino acid sequence of SEQ ID NOs: 15, 16, or 17 identified in Table 4 below are specific to CYP 3A5.

Figure 5A:
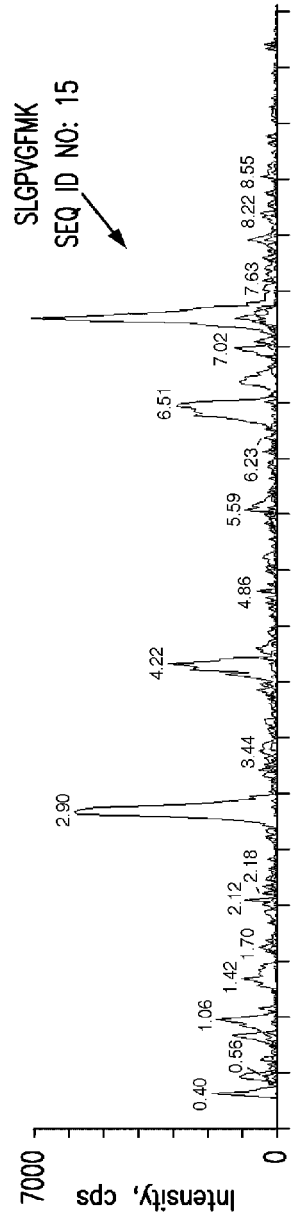
FIG. 5A shows an MRM analysis for 30 μl of a microsomal preparation for 3A5 (extracted ion chromatogram or +MRM (48 pairs)).
Figure 5B:
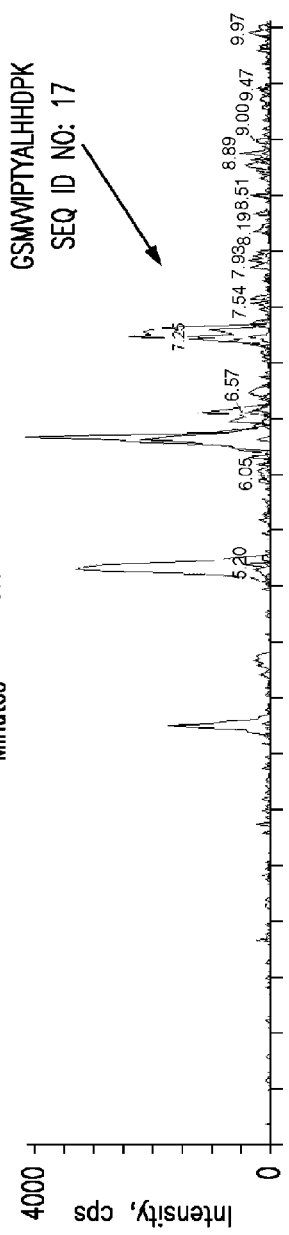
FIG. 5B shows an MRM analysis for 30 μl of a microsomal preparation for 3A5 (extracted ion chromatogram of +MRM (48 pairs)).
Figure 5C:
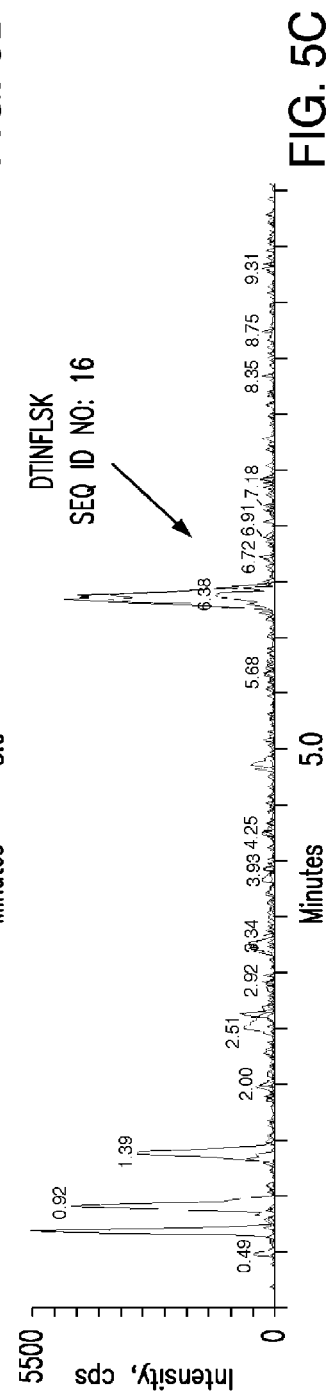
FIG. 5C shows an MRM analysis for 30 μl or a microsomal preparation for 3A5 (extracted ion chromatogram of +MRM (48 pairs)).

FIGS. 5A-5C show three different panes of a typical MRM analysis for CYP 3A5 from the microsomal preparation prepared as described herein. Each pane relates to specific transitions used for the particular peptide. The isolated peptides comprising the amino acid sequence of SEQ ID NOS: 15, 16, or 17 are specific to CYP 3A5.

According to various embodiments, the method can comprise determining an amount of CYP 2B6 in the sample by detecting an isolated peptide specific to cytochrome P450 (CYP) isoform CYP 2B6, for example, one or more of the isoforms comprising the amino acid sequence of SEQ ID NO: 1, SEQ ID NO: 2, or SEQ ID NO: 3 identified herein. The amount can be deter wined using a triple quadrupole instrument and Multiple Reaction Monitoring (MRM). In some embodiments, the isolated peptide can comprise the amino acid sequence of SEQ ID NO: 1 identified herein, and the method can comprise monitoring precursor-product ion pair transitions having an m/z value of about 548/911, 548/681, or 548/566, wherein the term "about" as used herein means within a range of +/− one (1) atomic mass unit. In some embodiments, the isolated peptide can comprise the amino acid sequence of SEQ ID NO: 2 identified herein, and the method can comprise monitoring precursor-product ion pair transitions having an m/z value of about 494/777, 494/437, or 494/874. In some embodiments, the isolated peptide can comprise the amino acid sequence of SEQ ID NO: 3 identified herein, and the method can comprise monitoring precursor-product ion pair transitions having an m/z value of about 421/508, 421/607, or 421/694. In some embodiments, the isolated peptide can comprise the amino acid sequence of SEQ ID NO: 4, and the method can comprise monitoring precursor-product ion pair transitions having an m/z value of about 479/499, 479/614, or 479/727.

According to various embodiments, the method can comprise determining an amount of CYP 3A4 in the sample by detecting an isolated peptide specific to cytochrome P450 (CYP) isoform CYP 3A4, comprising the amino acid sequence of SEQ ID NO: 5, SEQ ID NO: 6, or SEQ ID NO: 7 identified herein. The method can use, for example, a triple quadrupole instrument and Multiple Reaction Monitoring (MRM). In some embodiments, the isolated peptide can comprise the amino acid sequence of SEQ ID NO: 5 identified herein, and the method can comprise monitoring precursor-product ion pair transitions having an m/z value of about 440/549, 440/650, or 440/532. In some embodiments, the isolated peptide can comprise the amino acid sequence of SEQ ID NO: 6 identified herein, and the method can comprise monitoring precursor-product ion pair transitions having an m/z value of about 704/794, 704/929, 564/689, 564/745, or 564/790. In some embodiments, the isolated peptide can comprise the amino acid sequence of SEQ ID NO: 7 identified herein, and the method can comprise monitoring precursor-product ion pair transitions having an m/z value of about 798/819, 798/932, or 798/1004.

According to various embodiments, the method can comprise determining an amount of CYP 1A2 in the sample by detecting an isolated peptide specific to cytochrome P450 (CYP) isoform CYP 1A2, comprising the amino acid sequence of SEQ ID NO: 8, SEQ ID NO: 9, SEQ ID NO: 10, SEQ ID NO: 11, SEQ ID NO: 12, SEQ ID NO: 13, or SEQ ID NO: 14, identified herein. The method can use, for example, a triple quadrupole instrument and Multiple Reaction Monitoring (MRM).

In some embodiments, the isolated peptide can comprise the amino acid sequence of SEQ ID NO: 8 identified herein, and the method can comprise monitoring precursor-product ion pair transitions having an m/z value of about 432/636, 432/535, or 432/478. In some embodiments, the isolated peptide can comprise the amino acid sequence of SEQ ID NO: 9 identified herein, and the method can comprise monitoring precursor-product ion pair transitions having an m/z value of about 482/800, 482/628, or 482/743. In some embodiments, the isolated peptide can comprise the amino acid sequence of SEQ ID NO: 10 identified herein, and the method can comprise monitoring precursor-product ion pair transitions having an m/z value of about 491/721, 491/834, or 491/535. In some embodiments, the isolated peptide can comprise the amino acid sequence of SEQ ID NO: 11 identified herein, and the method can comprise monitoring precursor-product ion pair transitions having an m/z value of about 528/501, 528/614, or 528/727. In some embodiments, the isolated peptide can comprise the amino acid sequence of SEQ ID NO: 12 identified herein, and the method can comprise monitoring precursor-product ion pair transitions having an m/z value of about 571/783, 571/971, 571/1028, 381/587, 381/474, or 381/375. In some embodiments, the isolated peptide can comprise the amino acid sequence of SEQ ID NO: 13 identified herein, and the method can comprise monitoring precursor-product ion pair transitions having an m/z value of about 695/695, 695/837, or 695/950. In some embodiments, the isolated peptide can comprise the isolated peptide comprises the amino acid sequence of SEQ ID NO: 14 identified herein, and the method can comprise monitoring precursor-product ion pair transitions having an m/z value of about 536/795, 536/584, or 536/698.

According to various embodiments, the method can comprise determining an amount of CYP 3A5 in the sample by detecting an isolated peptide specific to cytochrome P450 (CYP) isoform CYP 3A5, comprising the amino acid sequence of SEQ ID NO: 15, SEQ ID NO: 16, or SEQ ID NO: 17 identified herein. The method can use, for example, a triple quadrupole instrument and Multiple Reaction Monitoring (MRM). In some embodiments, the isolated peptide can comprise an amino acid sequence of SEQ ID NO: 15 identified herein, and the method can comprise monitoring precursor-product ion pair transitions having an m/z value of about 468/581, 468/679, or 468/736. In some embodiments, the isolated peptide can comprise an amino acid sequence of SEQ ID NO: 16 identified herein, and the method can comprise monitoring precursor-product ion pair transitions baying an m/z value of about 470/494, 470/608, or 470/722. In some embodiments, the isolated peptide can comprise an amino acid sequence of SEQ ID NO: 17 identified herein, and the method can comprise monitoring precursor-product ion pair transitions having an m/z value of about 589/747, 589/696, or 589/647.

According to various embodiments of the present teachings, a kit is provided that can comprise one or more of the isolated peptides specific to one or more of cytochrome P450 (CYP) isoform CYP 2B6, CYP 3A4, CYP 1A2, and CYP 3A5. For example, the kit can comprise one or more isolated proteins specific to CYP 2B6, comprising the amino acid sequence of SEQ ID NO: 1, SEQ ID NO: 2, SEQ ID NO: 3, or SEQ ID NO: 4. The kit can comprise one or more isolated proteins specific to CYP isoform CYP 3A4, comprising the amino acid sequence of SEQ ID NO: 5, SEQ ID NO: 6, or SEQ ID NO: 7. The kit can comprise one or more isolated proteins specific to CYP isoform CYP 1A2, comprising the amino acid sequence of SEQ ID NO: 8, SEQ ID NO: 9, SEQ ID NO: 10. SEQ ID NO: 11, SEQ ID NO: 12, SEQ ID NO: 13, or SEQ ID NO: 14. The kit can comprise one or more isolated proteins specific to CYP isoform CYP 3A5, comprising the amino acid sequence of SEQ ID NO: 15, SEQ ID NO: 16, or SEQ ID NO: 17.

In some embodiments, the kit can comprise at least one isolated peptide specific to each of CYP isoforms CYP 2B6, CYP 3A4, CYP 1A2, and CYP 3A5. For example, the kit can comprise each of the isolated peptides of SEQ ID NOS: 1-17 identified herein, and further can comprise instructions for measuring Q1 and Q3 transition values for each of the isoform-specific peptides. The kit can comprise enzyme digestion components including buffers and enzymes, other buffers, and optionally other reagents and/or components. In some embodiments, the kit can comprise, for example, a homogeneous assay such that the user need only add a sample. In some embodiments, the kit can comprise calibration or normalization reagents or standards. Information pertaining to instrument settings that can or should be used to perform an assay can also be included in the kit. Information pertaining to sample preparation, operating conditions, volumetric amounts, temperature settings, and the like, can be included with the kit.

According to various embodiments, different transitions can be used to measure and benchmark assay results, depending on various factors. Accordingly, the kit can comprise different transition values and/or suggested settings, useful to make comparative measurements between a sample and one or more control reagents. The kit can include instructions to measure specific pairs of transition values, for example, the Q1/Q3 transition pair, or the values of one or more different transition pairs.

The kit can be packaged in a hermetically sealed container containing one or more regent vessels and appropriate instructions. An electronic medium can be included in the kit, having stored thereon electronic information pertaining to one or more assays, measurement values, transition pairs, operating instructions, software for carrying out operations, a combination thereof, or the like.

EXAMPLES

The present teachings can be even more fully understood with reference to the examples and =tilting data that follow. In the examples below and the results shown in the attached drawing figures, a CYP induction study was undertaken as follows.

Hepatocyte Treatment

Primary cultures of human hepatocytes were treated for 72 hours with the prototypical liver enzyme inducers 3-methylcholanthrene (3-MC, 2 µM), phenobarbital (PB, 1 mM), or rifampicin (RIF, 10 µM) to enhance the expression and activity of CYP1A2, CYP2B6, and CYP3A4, respectively. The CYP quantitation method of the present teachings was used to determine the amount of CYP in the sample after treatment with the liver enzyme inducers. In addition, CYP activity was measured by metabolite formation from selective substrates (phenacetin, bupropion and testosterone, respectively) and mRNA was measured by qRT-PCR (Taqman®, Applied Biosystems).

Microsome Preparation

Microsomal subcellular fractions were prepared by lysing treated hepatocytes in homogenization buffer (50 mM TRIS-HCl, pH 7.0, 150 mM KCl, 2 mM EDTA) followed by centrifugation at 9,000×g for 20 minutes at 4° C. The supernatant (S9 fraction) was then spun at 100,000×g for 60 minutes at 4° C. The resulting microsomal pellet was resuspended in 0.25 M sucrose and stored at −80° C. until analysis.

Tryptic Digestion

To 100 µl of each microsomal preparation, 5 µl of 2% SDS was added, followed by 10 µl of 50 mM TCEP and incubated at 60° C. for 1 hr. 5 µl of 0.1M MMTS was added and incubated at room temperature for 10 minutes. 100 µl of 100 mM TRIS (pH=8.50) was then added followed by 50 µg of trypsin and the resultant solution was digested overnight at 37° C. One (1) ng of each isotopically enriched synthetic peptide was added to the digest and analyzed by LC-MS.

Chromatography

Chromatography was performed using an Agilent 1100 system (Agilent of Santa Clara, Calif.) coupled to a C18 Jupiter Proteo 50×2.0 mm column (Phenomenex of Torrance, Calif.). The gradient was 5-40% B over 15 minutes with A consisting of 2% ACN, 0.1% formic and B consisting of 90% ACN, 10% H2O, 0.1% formic acid. Flow rate was 700 µL/min.

Mass Spectrometry

Samples were analyzed on a Applied Biosystems MDS SCIEX 4000 QTRAP™ LC/MS/MS system, using a Turbo V™ source and Analyst 1.5. For quantitation, scheduled MRM (sMRM) was used to maximize dwell time on each transition.

Data Processing

Quantitative data was processed using MultiQuant™ 1.2 software available from Applied Biosystems, LLC of Foster City, Calif.

Results

Figure 6:
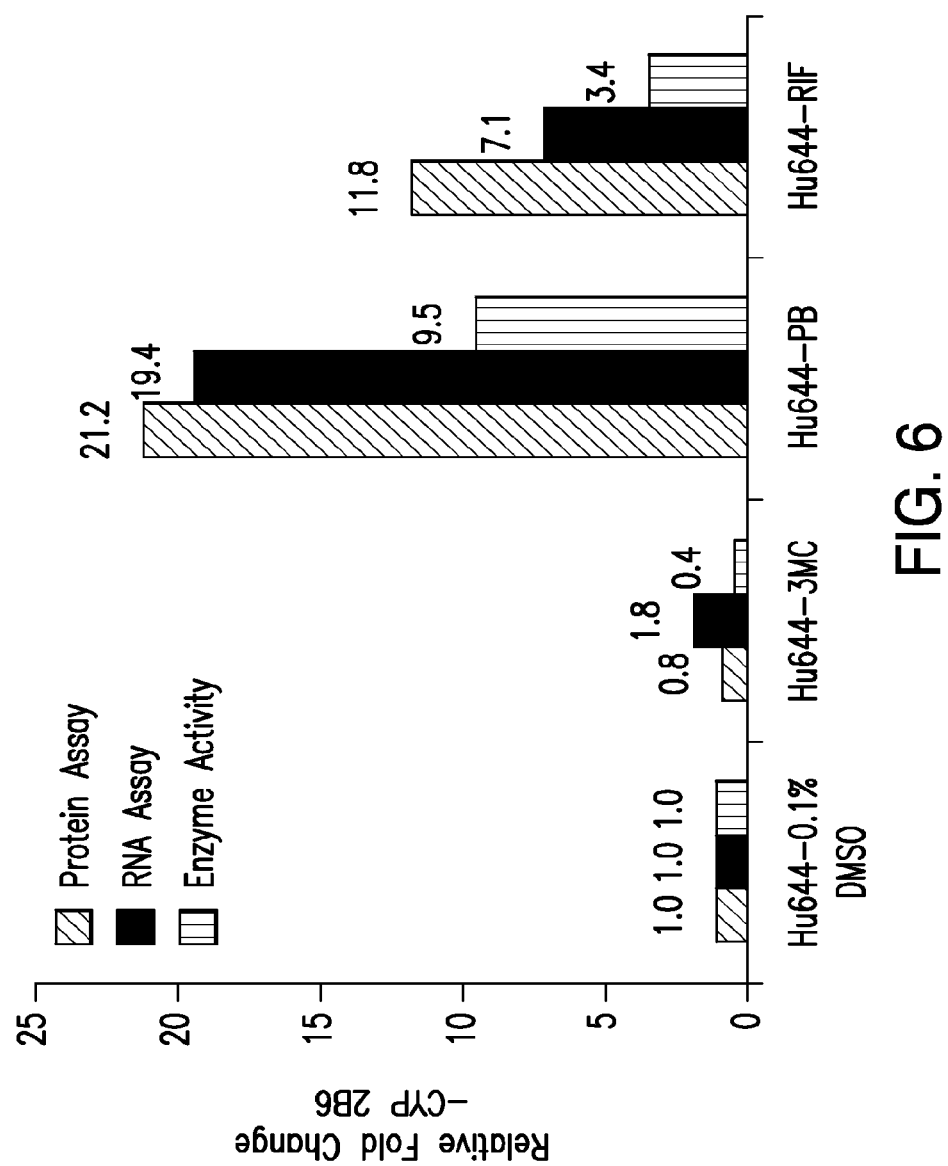
FIG. 6 shows a graph showing protein expression changes observed in a hepatocyte sample preparation treated with inducers for CYP 2B6, using RNA assays, enzyme activity assays and the protein quantitation method of the present teachings.

FIG. 6 is a graph comparing the changes in expression of CYP 2B6 observed using the RNA assay, the CYP activity assay (designated "enzyme activity assay" in the figures), and a CYP quantitation method of the present teachings (designated "protein assay" in the figures). The 3-MC is a vehicle control and induces basal levels of CYP 2B6. The PB is a prototypical inducer for CYP 2B6, by CAR nuclear receptor activation. The RIF is also a known inducer of CYP 2B6. As is shown, protein expression changes observed in the CYP activity assay and RNA assay generally mirror the expression changes observed using a CYP quantitation method of the present teachings.

Figure 7:
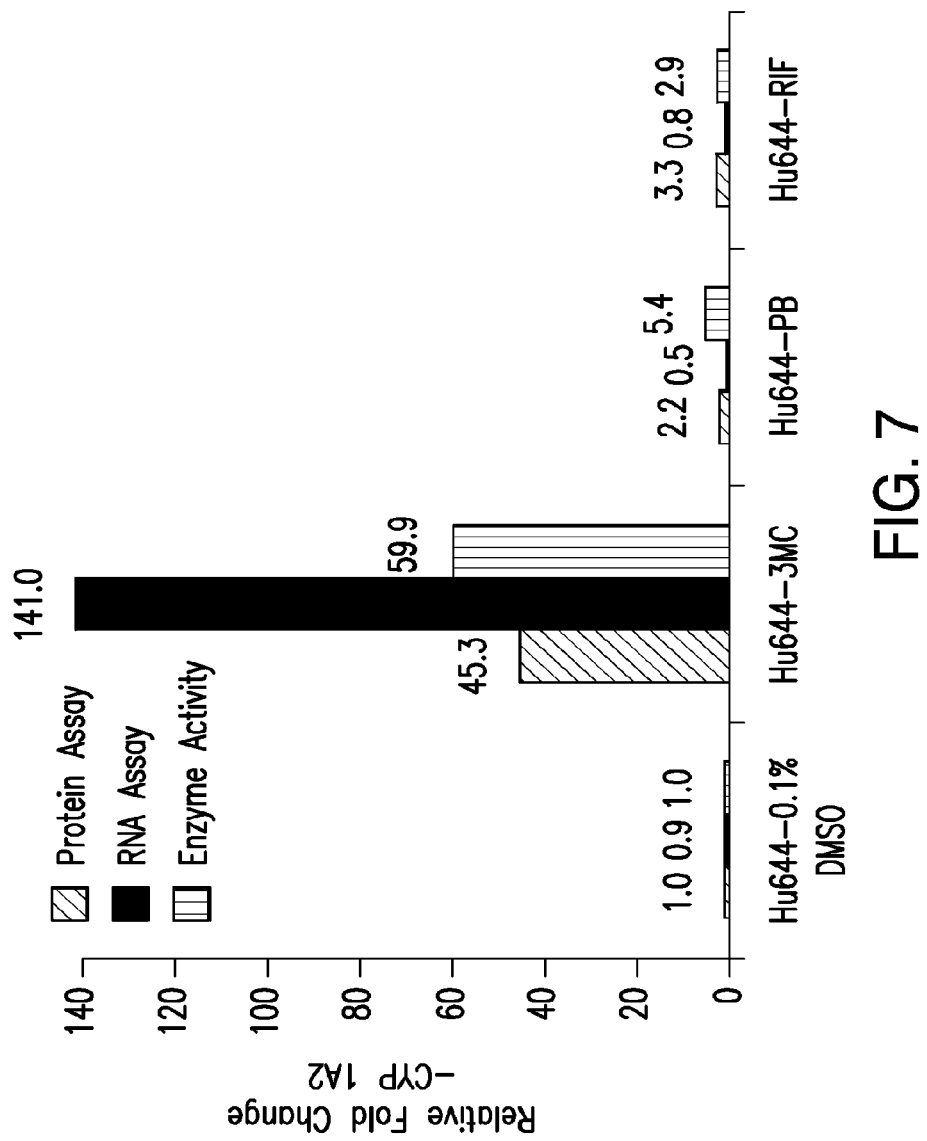
FIG. 7 shows a graph showing protein expression changes observed in a hepatocyte sample preparation treated with inducers for CYP 1A2, using RNA assays, enzyme activity assays and the protein quantitation method of the present teachings.

FIG. 7 is a graph comparing the changes in expression of CYP 1A2 observed using the RNA assay, the CYP activity assay (designated "enzyme activity assay" in the figures), and the CYP quantitation method of the present teachings (designated "protein assay" in the figures). The 3-MC is a prototypical inducer of CYP 1A2 by AhR nuclear receptor activation. The PB and RIP are vehicle controls inducing basal levels of 1A2, if any. As is shown, protein expression changes observed in the CYP activity assay and RNA assay generally mirror the expression changes observed using a CYP quantitation method of the present teachings, except that the RNA assay for the sample created with 3MC exhibits very high levels of RNA. The RNA assay cannot accurately quantify proteins because not all mRNA is converted to protein.

Figure 8:
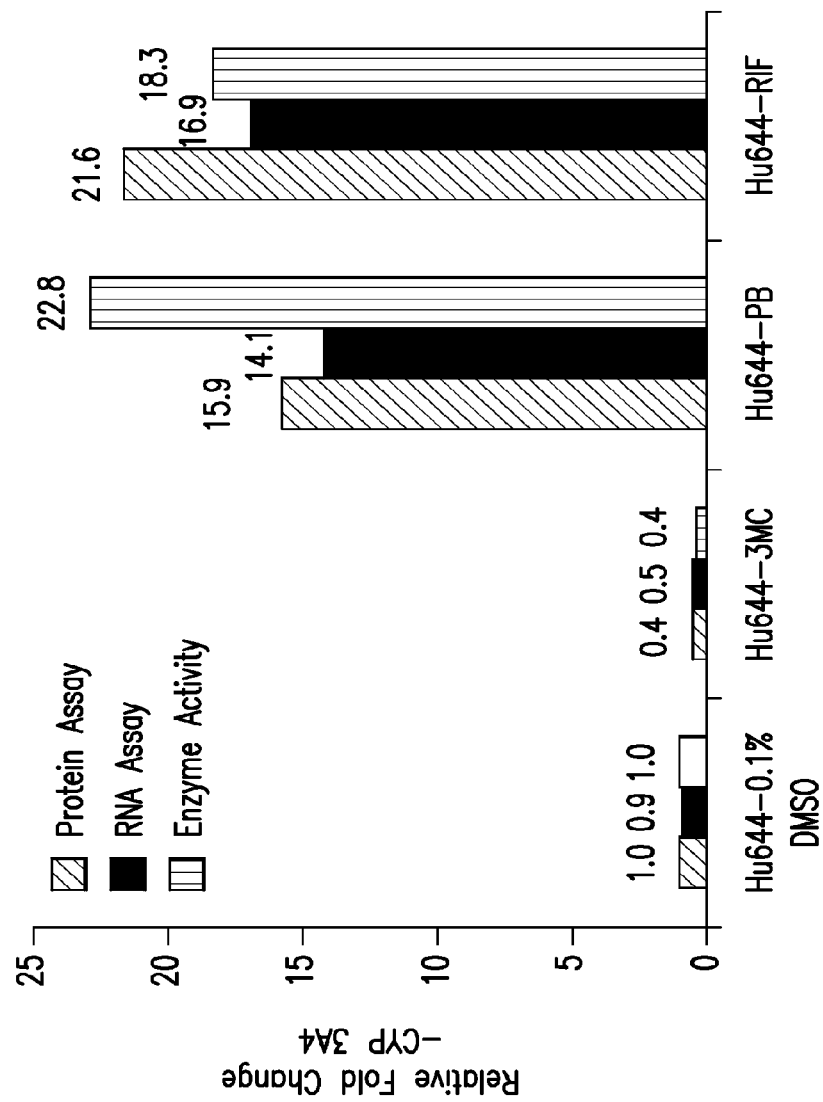
FIG. 8 shows a graph showing protein expression changes observed in a hepatocyte sample preparation treated with inducers for CYP 3A4, using RNA assays, enzyme activity assays and the protein quantitation method of the present teachings.

FIG. 8 is a graph comparing the changes in expression of CYP 3A4 observed using the RNA assay, the CYP activity assay (designated "enzyme activity assay" in the figures), and a CYP quantitation method of the present teachings (designated "protein assay" in the figures). The 3-MC minimally induces CYP 3A4. The PB significantly induces 3A4. The RIF is a prototypical inducer of CYP 3A4 by PXR nuclear receptor activation. As is shown, protein expression changes observed in the CYP activity assay and RNA assay generally mirror the expression changes observed using the CYP quantitation method of the present teachings.

Table 1 below shows sequences of the peptides determined, according to the present teachings, to be specific to cytochrome P450 (CYP) isoform CYP 2B6, along with their optimal MRM Q1, Q3 transitions. According to various embodiments, these observed peptides and transitions can be used to enable a reliable CYP quantitation of the isoform CYP 2B6.

TABLE 1

| 2B6 Human | Q1 | Q3 |
| --- | --- | --- |
| IAMVDPFFR (SEQ ID NO: 1) | 548.3 | 911.4 |
|  | 548.3 | 681.3 |
|  | 548.3 | 566.3 |
| IPPTYQIR (SEQ ID NO: 2) | 494.3 | 777.4 |
|  | 494.3 | 437.7 |
|  | 494.3 | 874.5 |
| FSVTTMR (SEQ ID NO: 3) | 421.2 | 508.4 |
|  | 421.2 | 607.3 |
|  | 421.2 | 694.4 |
| ETLDPSAPK (SEQ ID NO: 4) | 479.2 | 499.3 |
|  | 479.2 | 614.3 |
|  | 479.2 | 727.4 |

Table 2 below shows sequences of the peptides determined, according to the present teachings, to be specific to cytochrome P450 (CYP) isoform CYP 3A4, along with their optimal MRM Q1, Q3 transitions. According to various embodiments, these observed peptides and transitions can be used to enable a reliable CYP quantitation of the isoform CYP 3A4.

TABLE 2

| 3A4 Human | Q1 | Q3 |
| --- | --- | --- |
| EVTNFLR (SEQ ID NO: 5) | 439.7 | 549.3 |
|  | 439.7 | 650.5 |
|  | 439.7 | 532.3 |
| LSLGGLLQPEKPVVLK (SEQ ID NO: 6) | 704.4 | 794.5 |
|  | 704.4 | 929.8 |
| LSLGGLLQPEKPVVLK + 3 (SEQ ID NO: 6) | 564.3 | 789.5 |
|  | 564.3 | 745.9 |
|  | 564.3 | 689.4 |
| VWGFYDGQQPVLAITDPDMIK (SEQ ID NO: 7) | 798.4 | 819.4 |
|  | 798.4 | 932.5 |
|  | 798.4 | 1003.5 |

Table 3 below shows sequences of the peptides determined, according to the present teachings, to be specific to cytochrome P450 (CYP) isoform CYP 1A2, along with the optimal MRM Q1, Q3 transitions. According to various embodiments, these observed peptides and transitions can be used to enable a reliable CYP quantitation of the isoform CYP 1A2.

TABLE 3

| 1A2 Human | Q1 | Q3 |
|---|---|---|
| DITGALFK | 432.7 | 636.4 |
| (SEQ ID NO: 8) | 432.7 | 535.3 |
|  | 432.7 | 478.3 |
|  |  |  |
| YGDVLQIR | 482.3 | 800.5 |
| (SEQ ID NO: 9) | 482.3 | 628.4 |
|  | 482.3 | 743.4 |
|  |  |  |
| FLWFLQK | 491.3 | 721.4 |
| (SEQ ID NO: 10) | 491.3 | 834.4 |
|  | 491.3 | 535.3 |
|  |  |  |
| ASGNLIPQEK | 528.7 | 501.2 |
| (SEQ ID NO: 11) | 528.7 | 614.4 |
|  | 528.7 | 727.4 |
|  |  |  |
| IGSTPVLVLSR + 2 | 571.4 | 783.5 |
| (SEQ ID NO: 12) | 571.4 | 971.6 |
|  | 571.4 | 1028.6 |
|  |  |  |
| IGSTPVLVLSR + 3 | 381.1 | 587.4 |
| (SEQ ID NO: 12) | 381.1 | 474.3 |
|  | 381.1 | 375.2 |
|  |  |  |
| SPPEPWGWPLLGHVLYGK | 695.4 | 695.9 |
| (SEQ ID NO: 13) | 695.4 | 837.5 |
|  | 695.4 | 950.5 |
|  |  |  |
| YLPNPALQR | 536.3 | 795.4 |
| (SEQ ID NO: 14) | 536.3 | 584.3 |
|  | 536.3 | 698.4 |

10050 Table 4 below shows sequences of the peptides determined, according to the present teachings, to be specific to cytochrome P450 (CYP) isoform CYP 3A5, along with their optimal MRM Q1, Q3 transitions. According to various embodiments, these observed peptides and transitions can be used to enable a reliable CYP quantitation of the isoform CYP 3A5.

TABLE 4

| 3A5 | Q1 | Q3 |
|---|---|---|
| SLGPVGFMK | 468.5 | 581.5 |
| (SEQ ID NO: 15) | 468.5 | 678.1 |
|  | 468.5 | 735.5 |
|  |  |  |
| DTINFLSK | 469.5 | 494.3 |
| (SEQ ID NO: 16) | 469.5 | 608.4 |
|  | 469.5 | 721.5 |
|  |  |  |
| GSMVVIPTYALHHDPK | 589.2 | 746.5 |
| (SEQ ID NO: 17) | 589.2 | 696 |
|  | 589.2 | 646.5 |

Table 5 below shows sequences of the peptides along with their optimal MRM Q1, Q3 transitions for the housekeeping microsomal protein Microsomal GST. According to various embodiments, the concentration of this observed peptide is unaffected by drug incubation and thus the peptide can be useful as a normalization protein to enable reliable CYP quantitation.

TABLE 5

| Microsomal GST | Q1 | Q3 |
|---|---|---|
| DVNVENVNQQR | 657.8 | 758.3 |
| (SEQ ID NO: 18) | 657.8 | 887.5 |
|  | 657.8 | 545.3 |
|  |  |  |
| MYLLALK | 426.3 | 720.5 |
| (SEQ ID NO: 19) | 426.3 | 557.4 |
|  | 426.3 | 444.3 |
|  |  |  |
| NALLPEGIPSLLK | 682.9 | 1066.7 |
| (SEQ ID NO: 20) | 682.9 | 727.5 |
|  | 682.9 | 953.6 |

Table 6 below shows sequences of the peptides along with their optimal MRM Q1, Q3 transitions for the housekeeping microsomal protein Microsomal Triglyceride. According to various embodiments, the concentration of this observed peptide is unaffected by drug incubation and thus the peptide can be useful as a normalization protein to enable reliable CYP quantitation.

TABLE 6

| Microsomal Triglyceride | Q1 | Q3 |
|---|---|---|
| MMLMSTATAFYR | 711.8 | 829.4 |
| (SEQ ID NO: 21) | 711.8 | 916.2 |
|  | 711.8 | 1047.5 |

Table 7 below shows sequences of the peptides along with their optimal MRM Q1, Q3 transitions for the housekeeping microsomal protein Corticosteroid 11 beta. It should be understood that the Q1 and Q3 masses for the peptide of SEQ ID NO: 22 in Table 7 refers to the MMTS alkylated peptide and that changing to a different alkylating reagent will change the Q1, Q3 masses. In addition, alkylating reagents other than MMTS can be used. According to various embodiments, the concentration of this observed peptide is unaffected by drug incubation and thus the peptide can be useful as a normalization protein to enable reliable CYP quantitation.

TABLE 7

| Corticosteroid 11 beta | Q1 | Q3 |
|---|---|---|
| EECALEIIK | 547.3 | 615.4 |
| (SEQ ID NO: 22) | 547.3 | 686.4 |
|  | 547.3 | 835.4 |
|  |  |  |
| FALDGFFSSIR | 630.3 | 928.4 |
| (SEQ ID NO: 23) | 630.3 | 1041.5 |
|  | 630.3 | 813.4 |

The observed isoform-specific tryptic peptides that are detected using LC-MSMS analysis of microsomes, along with their optimal Q1, Q3 transitions, enable a method for CYP quantitation of the isoforms 1A2, 2B6, 3A4, and 3A5 without the need for any chemical labeling approaches.

Other embodiments of the present teachings will be apparent to those skilled in the art from consideration of the present specification and practice of the present teachings disclosed herein. It is intended that the present specification and examples be considered as exemplary only.

The invention claimed is:

1. A method for determining an amount of a CYP 3A5 isoform of cytochrome P450 (CYP) in a sample, said method comprising spiking into said sample a heavy form of a peptide having a peptide sequence of SEQ ID NO:15, and subjecting said sample to an analysis with a liquid chromatograph tandem mass spectrometer system, said system comprising a triple quadrupole instrument and Multiple Reaction Monitoring (MRM), said analysis comprising detecting at least one isolated peptide of CYP 3A5 having a peptide sequence of SEQ ID NO:15, said analysis is performed by monitoring a precursor-product ion pair transition having an m/z value of about 468/581, 468/679, or 468/736 in said system and processing data from said monitoring to determine said amount.

2. A method for screening a drug for cytochrome P450 (CYP) induction, comprising:

incubating the drug with a microsome-containing biological sample;

determining a quantitated value of at least one of a CYP 3A5 isoform in said drug incubated with the microsome-containing biological sample, said determining comprising, spiking into said drug incubated with the microsome-containing biological sample, a heavy form of a peptide having SEQ ID NO:15, subjecting said drug incubated with the microsome-containing biological sample to an analysis with a liquid chromatography tandem mass spectrometer system, said system comprising a triple quadrupole instrument and multiple reaction monitoring, said analysis comprising detecting an isolated peptide of said CYP 3A5 isoform, said analysis including monitoring a precursor-product ion pair transition having an m/z value of about 468/581, 468/679, or 468/736 in said system and processing data from said monitoring to determine said quantitated value;

comparing the quantitated value to a threshold value;

determining that the drug has an acceptable CYP induction potential when the quantitated value does not exceed the threshold value.

* * * * *

SEQUENCE LISTING

<160> NUMBER OF SEQ ID NOS: 23

<210> SEQ ID NO 1
<211> LENGTH: 9
<212> TYPE: PRT
<213> ORGANISM: Human

<400> SEQUENCE: 1

Ile Ala Met Val Asp Pro Phe Phe Arg
1               5

<210> SEQ ID NO 2
<211> LENGTH: 8
<212> TYPE: PRT
<213> ORGANISM: Human

<400> SEQUENCE: 2

Ile Pro Pro Thr Tyr Gln Ile Arg
1               5

<210> SEQ ID NO 3
<211> LENGTH: 7
<212> TYPE: PRT
<213> ORGANISM: Human

<400> SEQUENCE: 3

Phe Ser Val Thr Thr Met Arg
1               5

<210> SEQ ID NO 4
<211> LENGTH: 9
<212> TYPE: PRT
<213> ORGANISM: Human

<400> SEQUENCE: 4

Glu Thr Leu Asp Pro Ser Ala Pro Lys
1               5

<210> SEQ ID NO 5
<211> LENGTH: 7
<212> TYPE: PRT
<213> ORGANISM: Human

<400> SEQUENCE: 5

Glu Val Thr Asn Phe Leu Arg
1               5

<210> SEQ ID NO 6
<211> LENGTH: 16
<212> TYPE: PRT
<213> ORGANISM: Human

<400> SEQUENCE: 6

Leu Ser Leu Gly Gly Leu Leu Gln Pro Glu Lys Pro Val Val Leu Lys
1               5                   10                  15

<210> SEQ ID NO 7
<211> LENGTH: 21
<212> TYPE: PRT
<213> ORGANISM: Human

<400> SEQUENCE: 7

Val Trp Gly Phe Tyr Asp Gly Gln Gln Pro Val Leu Ala Ile Thr Asp
1               5                   10                  15

Pro Asp Met Ile Lys
            20

<210> SEQ ID NO 8
<211> LENGTH: 8
<212> TYPE: PRT
<213> ORGANISM: Human

<400> SEQUENCE: 8

Asp Ile Thr Gly Ala Leu Phe Lys
1               5

<210> SEQ ID NO 9
<211> LENGTH: 8
<212> TYPE: PRT
<213> ORGANISM: Human

<400> SEQUENCE: 9

Tyr Gly Asp Val Leu Gln Ile Arg
1               5

<210> SEQ ID NO 10
<211> LENGTH: 7
<212> TYPE: PRT
<213> ORGANISM: Human

<400> SEQUENCE: 10

Phe Leu Trp Phe Leu Gln Lys
1               5

<210> SEQ ID NO 11
<211> LENGTH: 10
<212> TYPE: PRT
<213> ORGANISM: Human

<400> SEQUENCE: 11

Ala Ser Gly Asn Leu Ile Pro Gln Glu Lys
1               5                   10

<210> SEQ ID NO 12
<211> LENGTH: 11
<212> TYPE: PRT
<213> ORGANISM: Human

<400> SEQUENCE: 12

Ile Gly Ser Thr Pro Val Leu Val Leu Ser Arg
1               5                   10

<210> SEQ ID NO 13
<211> LENGTH: 19
<212> TYPE: PRT
<213> ORGANISM: Human

<400> SEQUENCE: 13

Ser Pro Pro Glu Pro Trp Gly Trp Pro Leu Leu Gly His Val Leu Thr
1               5                   10                  15

Leu Gly Lys

<210> SEQ ID NO 14
<211> LENGTH: 9
<212> TYPE: PRT
<213> ORGANISM: Human

<400> SEQUENCE: 14

Tyr Leu Pro Asn Pro Ala Leu Gln Arg
1               5

<210> SEQ ID NO 15
<211> LENGTH: 9
<212> TYPE: PRT
<213> ORGANISM: Human

<400> SEQUENCE: 15

Ser Leu Gly Pro Val Gly Phe Met Lys
1               5

<210> SEQ ID NO 16
<211> LENGTH: 8
<212> TYPE: PRT
<213> ORGANISM: Human

<400> SEQUENCE: 16

Asp Thr Ile Asn Phe Leu Ser Lys
1               5

<210> SEQ ID NO 17
<211> LENGTH: 16
<212> TYPE: PRT
<213> ORGANISM: Human

<400> SEQUENCE: 17

Gly Ser Met Val Val Ile Pro Thr Tyr Ala Leu His His Asp Pro Lys
1               5                   10                  15

<210> SEQ ID NO 18
<211> LENGTH: 11
<212> TYPE: PRT
<213> ORGANISM: Human

<400> SEQUENCE: 18

Asp Val Asn Val Glu Asn Val Asn Gln Gln Arg
1               5                   10

<210> SEQ ID NO 19
<211> LENGTH: 7
<212> TYPE: PRT
<213> ORGANISM: Human

<400> SEQUENCE: 19

Met Tyr Leu Leu Ala Leu Lys
1               5

<210> SEQ ID NO 20
<211> LENGTH: 13
<212> TYPE: PRT
<213> ORGANISM: Human

<400> SEQUENCE: 20

Asn Ala Leu Leu Pro Glu Gly Ile Pro Ser Leu Leu Lys
1               5                   10

<210> SEQ ID NO 21
<211> LENGTH: 12
<212> TYPE: PRT
<213> ORGANISM: Human

<400> SEQUENCE: 21

Met Met Leu Met Ser Thr Ala Thr Ala Phe Tyr Arg
1               5                   10

```
<210> SEQ ID NO 22
<211> LENGTH: 9
<212> TYPE: PRT
<213> ORGANISM: Human

<400> SEQUENCE: 22

Glu Glu Cys Ala Leu Glu Ile Ile Lys
1               5

<210> SEQ ID NO 23
<211> LENGTH: 11
<212> TYPE: PRT
<213> ORGANISM: Human

<400> SEQUENCE: 23

Phe Ala Leu Asp Gly Phe Phe Ser Ser Ile Arg
1               5                   10
```